United States Patent
Yamane et al.

(10) Patent No.: US 8,384,888 B2
(45) Date of Patent: Feb. 26, 2013

(54) MASK DEFECT MEASUREMENT METHOD, MASK QUALITY DETERMINATION AND METHOD, AND MANUFACTURING METHOD OF SEMICONDUCTOR DEVICE

(75) Inventors: Takeshi Yamane, Tsukuba (JP); Tsuneo Terasawa, Tokyo (JP); Toshihiko Tanaka, Tokyo (JP)

(73) Assignees: Kabushiki Kaisha Toshiba, Tokyo (JP); Renesas Technology Corp., Tokyo (JP)

( * ) Notice: Subject to any disclaimer, the term of this patent is extended or adjusted under 35 U.S.C. 154(b) by 514 days.

(21) Appl. No.: 12/750,396

(22) Filed: Mar. 30, 2010

(65) Prior Publication Data
US 2011/0043811 A1 Feb. 24, 2011

(30) Foreign Application Priority Data
Aug. 18, 2009 (JP) ................. 2009-189250

(51) Int. Cl.
*G01N 21/00* (2006.01)
(52) U.S. Cl. .................................... 356/237.2
(58) Field of Classification Search .......... None
See application file for complete search history.

(56) References Cited

U.S. PATENT DOCUMENTS 7,171,034 B2 * 1/2007 Wu et al. ........... 382/144
7,388,978 B2 * 6/2008 Duvdevani et al. ........... 382/145
7,436,507 B2 * 10/2008 Moribe ................ 356/237.4

FOREIGN PATENT DOCUMENTS

| JP | 2003-004654 | 1/2003 |
| JP | 2003-114200 | 4/2003 |
| JP | 2006-080437 | 3/2006 |
| JP | 2007-171640 | 7/2007 |

\* cited by examiner

*Primary Examiner* — Tu Nguyen
(74) *Attorney, Agent, or Firm* — Finnegan, Henderson, Farabow, Garrett & Dunner, L.L.P.

(57) ABSTRACT

A method for measuring a shape of a phase defect existing on an exposure mask includes making inspection light incident on the mask, measuring the intensity of light scattered in an angular range in which the width of an scattering area on the phase defect can be predicted, calculating a radius of the phase defect based on the measured scattered light intensity, changing the angular range of scattered light to be measured, remeasuring scattered light intensity in the thus changed angular range, and calculating a scattering cross-sectional area based on the scattered light intensity obtained by remeasurement. A process of remeasuring the scattered light intensity and calculating the scattering cross-sectional area is repeatedly performed until the remeasured scattered light intensity is saturated and the shape of the phase defect is determined by using the calculated radius of the phase defect and each of the calculated scattering cross-sectional areas.

19 Claims, 5 Drawing Sheets

MASK DEFECT MEASUREMENT METHOD, MASK QUALITY DETERMINATION AND METHOD, AND MANUFACTURING METHOD OF SEMICONDUCTOR DEVICE

CROSS-REFERENCE TO RELATED APPLICATIONS

This application is based upon and claims the benefit of priority from prior Japanese Patent Application No. 2009-189250, filed Aug. 18, 2009, the entire contents of which are incorporated herein by reference.

BACKGROUND OF THE INVENTION

1. Field of the Invention

This invention relates to a mask defect measurement method and mask quality determination method for measuring a phase defect of a semiconductor exposure mask or the like used for exposure by the use of EUV in a blank mask state. In addition, the present invention relates to a manufacturing method of the semiconductor device that uses the above-mentioned method.

2. Description of the Related Art

A semiconductor exposure mask used for exposure by the use of EUV is a reflecting mask. The mask has a structure in which two types of layers having different reflectances called a multilayered film are alternately laminated on a glass substrate, a film called an absorber is formed on the multilayered film and then a circuit pattern is formed by processing the absorber. If particles are present on the glass substrate when the multilayered film is formed, the multilayered film formed thereon is locally upheaved or subsided. Since an area (phase defect) in which the phase of the reflected light is disturbed occurs, there occurs a problem that the area will be transferred onto a wafer at the exposure time. Therefore, it is necessary to check whether a phase defect is present or not in a state called a blank mask state set before the absorber is formed.

As the technique for checking the presence of a phase defect of the blank mask, a method for specifying the position of the defect by irradiating the blank mask with EUV and detecting scattered light produced when a defect is present on the blank mask is proposed (for example, see Jpn. Pat. Appln. KOKAI Publication No. 2003-114200). However, since the size of a phase defect is generally considerably smaller than that of a CCD pixel, it is difficult to specify the shape of the phase defect based on a detected signal. If the CCD pixel is formed sufficiently small, the minimum size of a defect whose shape can be specified becomes smaller. However, since the time required for checking phase defects on the entire surface of the mask is inversely proportional to the size of the CCD pixel, the checking cost will increase. Further, even if the CCD pixel is made small, it is difficult to obtain information associated with the height of the phase defect.

Further, a method for focusing reflected light of light incident on the blank mask onto a detecting portion, blocking a portion of the reflected light by means of a shielding plate disposed in an intermediate portion of the optical path and detecting irregularity of the blank mask based on the intensity of the reflected light obtained by the detecting portion is proposed (for example, see Jpn. Pat. Appln. KOKAI Publication No. 2003-4654). With this technique, the defect detecting operation and the shape specifying operation can be performed by means of the same device. However, only whether the defect is concave or convex can be determined and a problem that the shape measurement cannot be sufficiently made occurs.

Further, a defect checking method of EUV mask blanks by using a Schwarzschild optics is proposed (for example, see Jpn. Pat. Appln. KOKAI Publication No. 2007-171640). However, this technique is to output the importance of a defect (the level of a risk of transfer) based on the angular distribution of the intensity of scattered light and is not a method for specifying the shape of a defect. That is, the technique is to output a proportion of the shapes of defects to be transferred among the shapes of defects estimated based on the angular distribution. For example, if half of the estimated shapes of defects are transferred, the transfer risk is set to 50% and if none of the estimated shapes of defects is transferred, the transfer risk is set to 0%. Therefore, in a case other than the risk of 0 or 100%, it becomes impossible to correctly determine whether the defect will be transferred or not.

BRIEF SUMMARY OF THE INVENTION

According to one aspect of this invention, there is provided a mask defect measurement method for measuring a shape of a phase defect existing on an exposure mask, comprising previously deriving an angular range in which width of a scattering area on the phase defect is predictable within an angular range in which inspection light having a desired wavelength incident on the mask is scattered by the phase defect on the mask and measuring intensity of light scattered in the angular range; calculating a radius of the phase defect based on the measured scattered light intensity by using a previously set relational expression; changing the angular range of scattered light to be measured and remeasuring scattered light intensity in the changed angular range; calculating a scattering cross-sectional area based on the remeasured scattered light intensity by using a relational expression of the predetermined scattered light intensities and scattering cross-sectional areas; repeatedly performing a process of remeasuring the scattered light intensity and calculating the scattering cross-sectional area until the remeasured scattered light intensity is saturated; and determining a shape of the phase defect on the mask by using the calculated radius of the phase defect and each of the calculated scattering cross-sectional areas according to a predetermined phase defect shape model.

According to another aspect of this invention, there is provided a mask defect measurement method for measuring a position and shape of a phase defect existing on an exposure mask, comprising scanning light on the mask to detect a position in which scattered light is emitted from the mask as the position of the phase defect; previously deriving an angular range in which width of a scattering area on the phase defect is predictable within an angular range in which inspection light having a desired wavelength incident on the mask is scattered by the phase defect on the mask and measuring intensity of light scattered in the angular range when the inspection light is made incident on the mask in the detected defect position; calculating a radius of the phase defect based on the measured scattered light intensity by using a previously set relational expression; changing the angular range of scattered light to be measured and remeasuring scattered light intensity in the changed angular range; calculating a scattering cross-sectional area based on the remeasured scattered light intensity by using a relational expression of the predetermined scattered light intensities and scattering cross-sectional areas; repeatedly performing a process of remeasuring the scattered light intensity and calculating the scattering cross-sectional area until the remeasured scattered light intensity is saturated; and determining a shape of the phase defect on the mask by using the calculated radius of the phase defect and each of the calculated scattering cross-sectional areas according to a predetermined phase defect shape model.

According to another aspect of this invention, there is provided a mask quality determination method, comprising previously deriving an angular range in which width of a scattering area on a phase defect is predictable within an angular range in which inspection light having a desired wavelength incident on a mask is scattered by the phase defect on the mask and measuring intensity of light scattered in the angular range; calculating a radius of the phase defect based on the measured scattered light intensity by using a previously set relational expression; changing the angular range of scattered light to be measured and remeasuring scattered light intensity in the changed angular range; calculating a scattering cross-sectional area based on the remeasured scattered light intensity by using a relational expression of the predetermined scattered light intensities and scattering cross-sectional areas; repeatedly performing a process of remeasuring the scattered light intensity and calculating the scattering cross-sectional area until the remeasured scattered light intensity is saturated; determining a shape of the phase defect on the mask by using the calculated radius of the phase defect and each of the calculated scattering cross-sectional areas according to a predetermined phase defect shape model; and determining quality of the mask by comparing the determined defect shape with a predetermined defect shape permissible range.

DETAILED DESCRIPTION OF THE INVENTION

Before explaining embodiments of the present invention, the basic principle of this invention is described.

Figure 1:
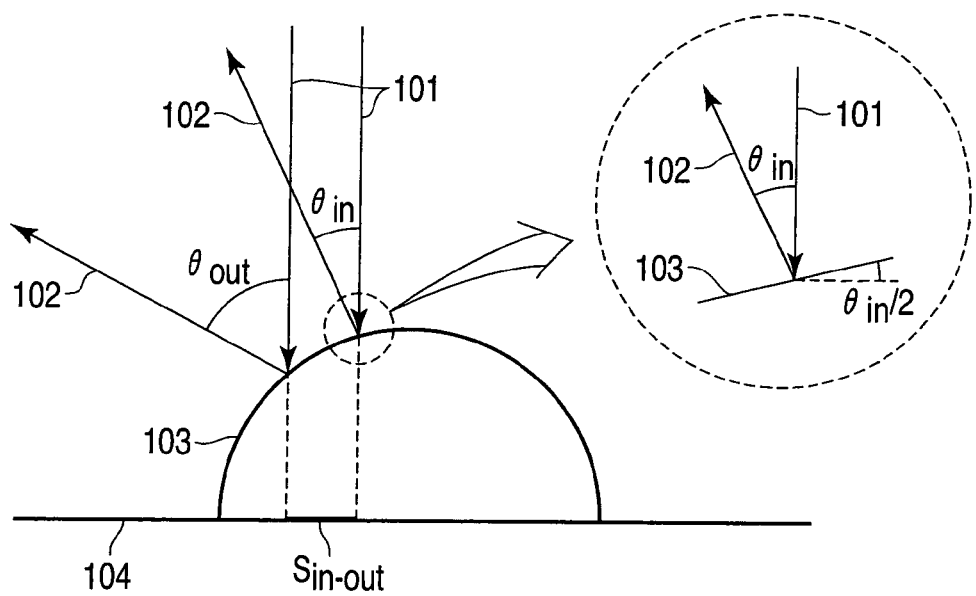
FIG. 1 is a diagram showing the relationship between the tilt angle of a phase defect on a mask, scattering cross-sectional area and the radiation angle of scattered light.

FIG. 1 is a diagram showing the relationship between the tilt angle of a phase defect on a blank mask, scattering cross-sectional area and the radiation angle of scattered light. The blank mask is used as a base body of a reflecting semiconductor exposure mask used for exposure by the use of EUV and is obtained by alternately laminating two types of layers having different reflectances on a glass substrate.

When inspection light 101 having a given wavelength is made incident on a mask (blank mask) 104 in a vertical direction, light 102 scattered by a phase defect 103 is regarded as a set of reflected light in an infinitesimal area. As shown in FIG. 1, an angle made between the incident light 101 and the reflected light 102 is twice the tilt angle of each infinitesimal area. The intensity I of the reflected light 102 can be expressed as follows by using an area S (hereinafter referred to as the scattering cross-sectional area) obtained by projecting the infinitesimal area onto a surface that is perpendicular to the incident direction, reflectance R and incident light intensity $I_i$ for each unit area.

$$I = S \times R \times I_i \quad (1)$$

The intensity of scattered light having a radiation angle not smaller than $\theta_{in}$ and not larger than $\theta_{out}$ is measured by blocking scattered light having a radiation angle smaller than $\theta_{in}$ by means of a central shielding portion and blocking scattered light having a radiation angle larger than a given radiation angle $\theta_{out}$ by means of a variable aperture stop. A scattering cross-sectional area $S_{in\text{-}out}$ of the infinitesimal area having a tilt angle ranging from $\theta_{in}/2$ to $\theta_{out}/2$ can be derived by the use of the thus obtained intensity and Equation (1).

The operation of changing $\theta_{out}$ as desired by changing the numerical aperture of the variable aperture stop, deriving a scattering cross-sectional area based on Equation (1) and deriving a combination of the tilt angular range of the infinitesimal area and the scattering cross-sectional area is performed. If the above operation is performed twice or more, the shape of the phase defect can be determined based on the thus obtained combination and a previously determined shape model.

Next, this invention is explained in detail with reference to embodiments shown in the accompanying drawings.

(First Embodiment)

Figure 2:
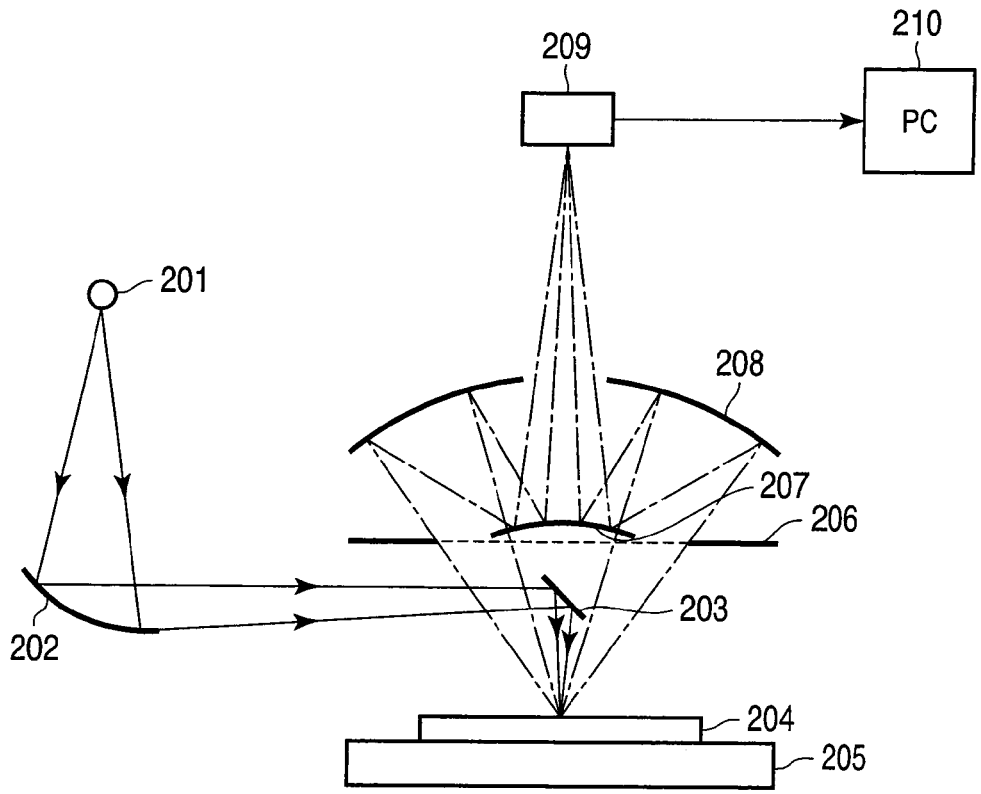
FIG. 2 is a diagram showing the configuration of a device that performs a mask defect shape measurement method according to a first embodiment.

FIG. 2 is a diagram showing the configuration of a device that performs a mask defect shape measurement method according to a first embodiment of this invention.

A mask (blank mask) 204 is set on a mask stage 205 that moves the mask 204 to a desired position. A plane mirror 203 is provided above the mask 204 and mask stage 205. Light emitted from a light source 201 that radiates EUV is converged by an elliptical mirror 202, reflected by the plane mirror 203 and irradiated onto the mask 204 in a direction perpendicular to the mask surface. Light irradiation at this time is batch irradiation for an area larger than the size of an estimated defect.

A variable aperture stop 206 that blocks scattered light whose radiation angle exceeds a desired angle of light scattered by the mask 204 and in which the desired angle can be changed is provided above the plane mirror 203. The shape of the opening of the variable aperture stop 206 is a circle with the set position of the plane mirror 203 set as a center.

A shielding portion (convex mirror) 207 that blocks scattered light having a radiation angle smaller than a desired angle of light scattered by the mask 204 and focuses scattered light that has passed through the variable aperture stop 206 together with the concave mirror that will be described later is provided above the plane mirror 203. That is, the concave mirror 207 is disposed directly above the central point of the position of light irradiation by the plane mirror 203 and the back surface of the plane mirror 203 functions as a shielding portion.

A concave mirror 208 that focuses scattered light that has passed through the variable aperture stop 206 is provided above the variable aperture stop 206 and convex mirror 207. Scattered light reflected from the concave mirror 208 is further reflected from the convex mirror 207 and is focused on a detector 209.

For example, the detector 209 is a CDD image-sensing element and a detection output of the detector 209 is input to a personal computer 210. Then, the intensity of the scattered light detected by the detector 209 is retrieved by the personal computer 210, the tilt range of a scattered portion and the scattering cross-sectional area are calculated and the shape of the phase defect is determined by using a shape model of the phase defect.

Figure 3:
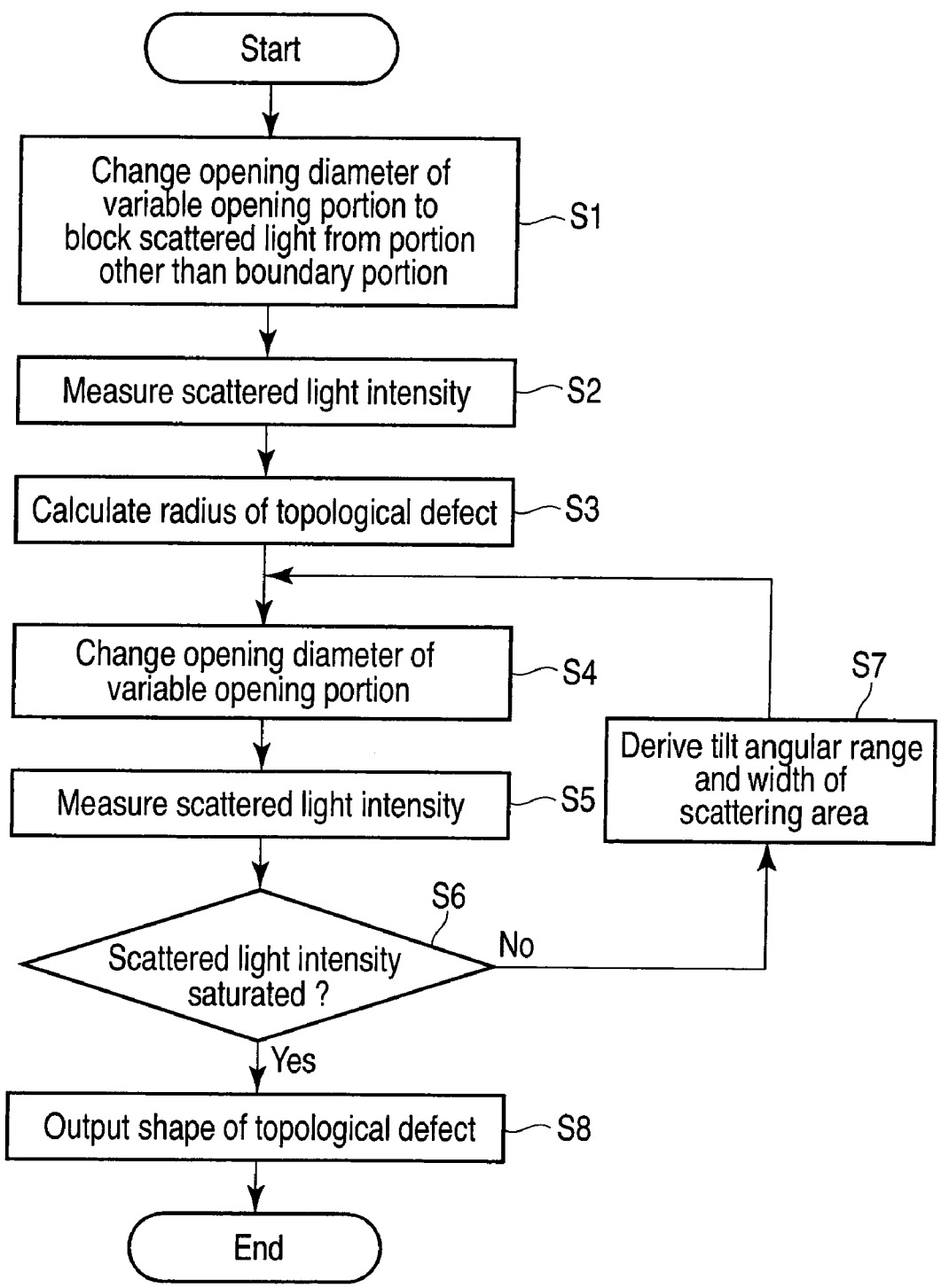
FIG. 3 is a flowchart for illustrating the mask defect shape measurement method according to the first embodiment.

Next, the flowchart of the mask defect shape measurement method performed by means of the above device is illustrated in FIG. 3 and explained below with reference to FIG. 3.

Figure 4:
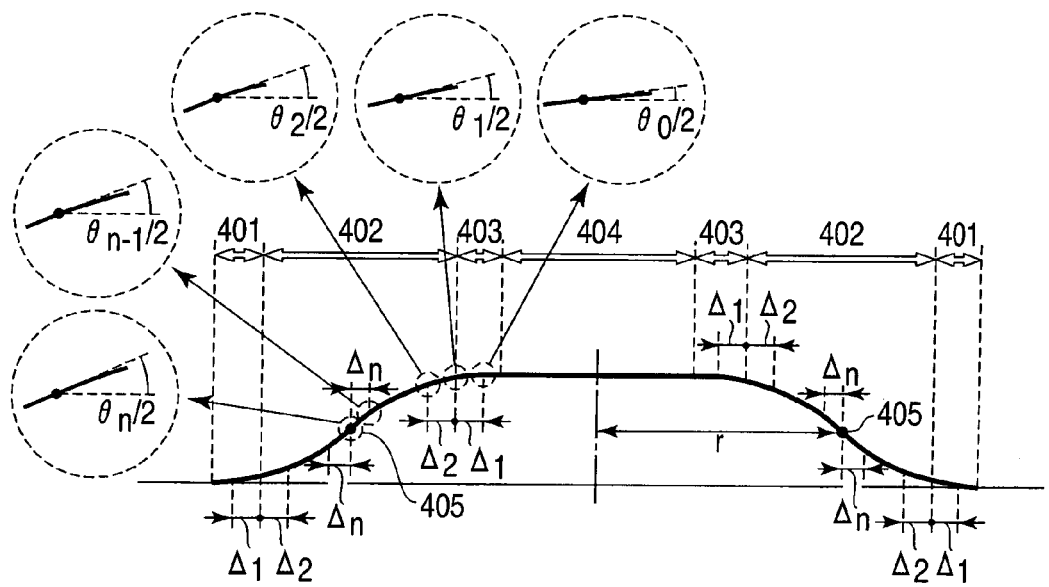
FIG. 4 is a diagram showing a cross-sectional shape of a previously estimated phase defect.
Figure 5:
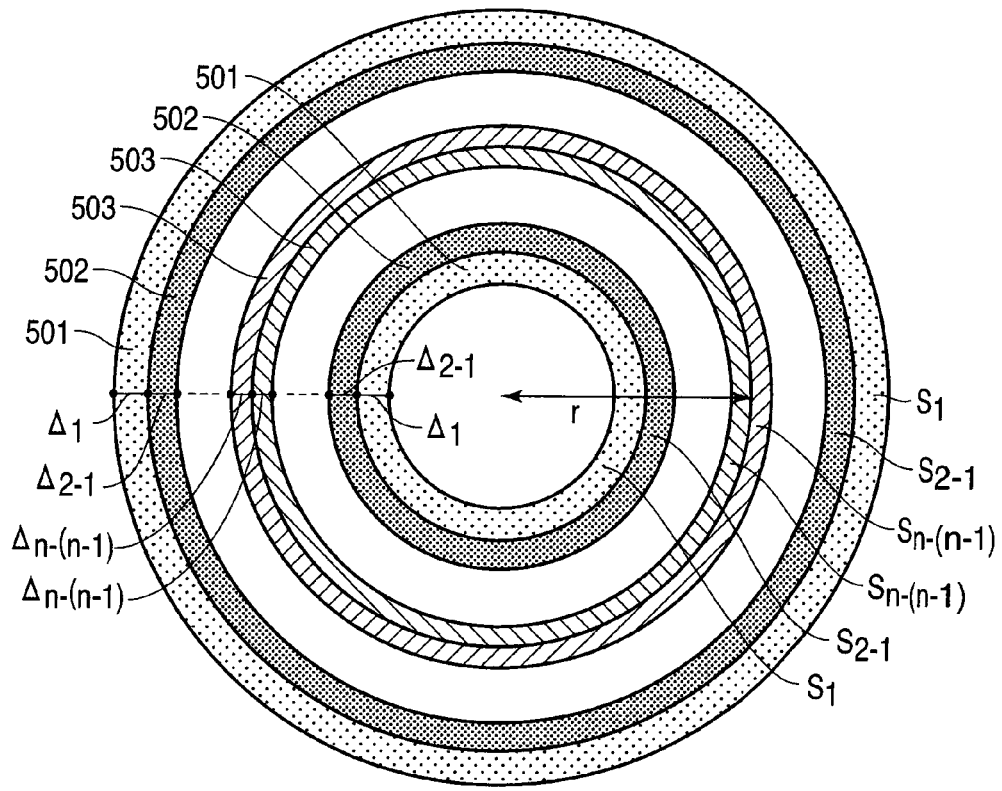
FIG. 5 is a contour diagram showing height information of a previously estimated phase defect.

As an example of the phase defect on the surface of a multilayered film, a shape shown in FIGS. 4 and 5 is assumed. FIG. 4 is a diagram showing a previously estimated phase defect cross-sectional shape and FIG. 5 is a contour diagram showing height information of a previously assumed phase defect. The cross-sectional shape includes boundary portions 401, 403, sidewall portion 402 and flat portion 404. It is assumed that the boundary portions 401, 403 have known shapes that are inverted by 180 degrees from each other and the width and height of the sidewall portion 402 and the width of the flat portion 404 are unknown. The tilt angles of the boundary portions 401, 403 and the sidewall portion 402 are set to be maximum ($\theta_n/2$) at the sidewall center 405 and uniformly and gently decrease towards the upper portion or lower portion.

First, scattered light produced only by the boundary portion is measured as follows. Since scattered light whose radiation angle is smaller than $\theta_0$ is blocked by the shielding portion 207, scattered light intensity $I_1$ whose radiation angle ranges from $\theta_0$ to $\theta_1$ is measured by changing the numerical aperture of the variable aperture stop 208 (step S1 in the flowchart of FIG. 3) (step S2). Then, a scattering cross-sectional area $S_1$ of an area 501 whose tilt angle ranges from $\theta_0/2$ to $\theta_1/2$ is derived by means of Equation (1). At this time, the proportional coefficient of the scattered light intensity and scattering cross-sectional area is experimentally and previously derived and the cross-sectional area $S_1$ can be derived from the scattered light intensity $I_1$ by the use of the proportional coefficient. Since area 501 is a part of the boundary portion, the width $\Delta_1$ thereof is assumed to be already known. The radius r of the phase defect can be derived as follows by using the thus obtained cross-sectional area $S_1$ and width $\Delta_1$ (step S3).

$$r = S_1/(4\pi\Delta_1) \quad (2)$$

That is, the total area $S_1$ of two areas 501 can be expressed as follows if areas 501 are positioned separately at the same distance $\alpha$ inwardly and outwardly with respect to the point of the radius r.

$$S_1 = 2\pi(r+\alpha)\Delta_1 + 2\pi(r-\alpha)\Delta_1 = 4\pi r\Delta_1$$

Therefore, the radius r can be derived by means of Equation (2).

Next, the numerical aperture of the variable aperture stop 206 is changed (step S4) and scattered light intensity $I_2$ having a radiation angle of $\theta_0$ to $\theta_2$ is remeasured (step S5). As a result, scattered light intensity $I_{2-1}$ having a radiation angle exceeding $\theta_1$ but not larger than $\theta_2$ is derived by ($I_2-I_1$). Then, a scattering cross-sectional area $S_{2-1}$ of area 502 whose tilt angle exceeds $\theta_1/2$ and is not larger than $\theta_2/2$ is derived from the thus derived intensity $I_{2-1}$ by means of Equation (1). Width $\Delta_{2-1}$ of area 502 is derived from the radius r derived from the scattered light intensity $I_1$ and the thus derived scattering cross-sectional area $S_{2-1}$ based on Equation (2). Since the maximum tilt angle is $\theta_n/2$, the phenomenon that the scattered light intensity is saturated in a range of the radiation angle of not smaller than $\theta_n$ is utilized. Then, a process of changing the numerical aperture of the variable aperture stop and deriving a scattering cross-sectional area and width is repeatedly performed until the thus derived scattered light intensity is saturated (steps S6, S7).

Figure 6:
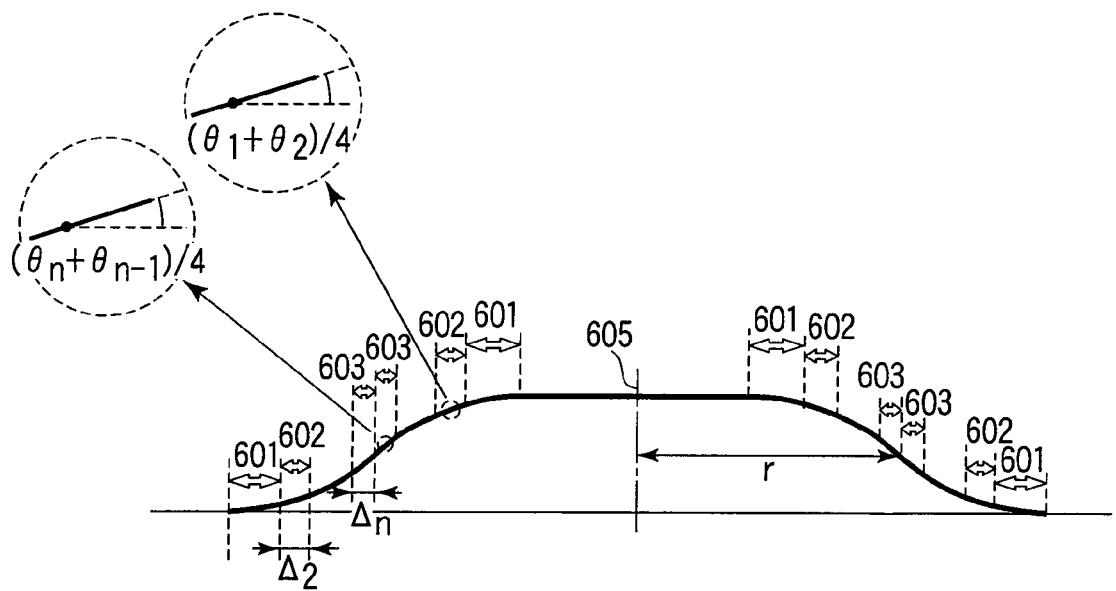
FIG. 6 is a diagram showing a cross-sectional shape of a phase defect obtained in the first embodiment.

A cross-sectional shape of the phase defect is output as follows based on a combination of the thus derived tilt angular range and width (step S8). More specifically, since the cross-sectional shape having the tilt angle of $\theta_1/2$ or less is already known, an area whose tilt angle exceeds $\theta_1/2$ and is not larger than $\theta_2/2$ can be expressed by a straight line having a tilt angle of $(\theta_1+\theta_2)/4$ and width $\Delta_{2-1}$. Likewise, an area whose tilt angle exceeds $\theta_{n-1}/2$ is not larger than $\theta_n/2$ can be expressed by a straight line having a tilt angle of $(\theta_{n-1}+\theta_n)/4$ and width $\Delta_{n-(n-1)}$. As result, cross-sectional shapes 601, 602, 603 shown in FIG. 6 are obtained. Then, shapes obtained by rotating the cross-sectional shapes 601, 602, 603 with the central axis 605 set as a center are output as shapes of the phase defect.

In the above example, the surface projection of the blank mask is assumed, but in a case of surface depression obtained by vertically inverting the drawing of FIG. 4, shapes can be derived by means of the same method.

Figure 7:
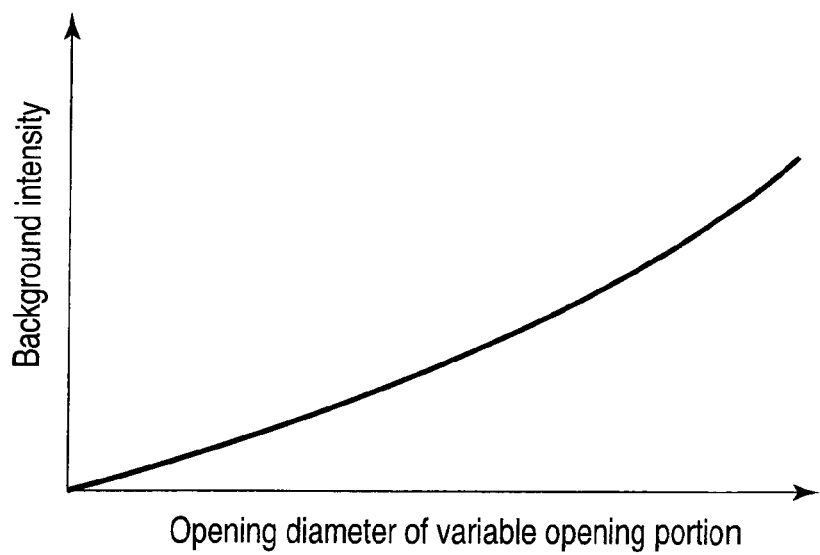
FIG. 7 is a diagram showing the relationship between the background intensity and numerical aperture.

Weak scattered light (background) may be produced even in a case of no defect due to minute projection and depression or the like called surface roughness of the blank mask. The intensity of the background may vary depending on a variation in the numerical aperture of the variable aperture stop. In such a case, more precise measurement can be made by previously deriving the relationship between the background intensity and the variable aperture stop as shown in FIG. 7 and using a value obtained by subtracting the background intensity from the measured scattered light intensity as actual scattered light intensity.

Thus, according to this embodiment, the shape of a phase defect that is extremely small in comparison with the CCD pixel size can be measured and the effect of lowering the cost for inspection can be obtained. That is, the surface shape of a phase defect existing on the exposure mask can be efficiently measured and it can contribute to enhancement of the production efficiency of exposure masks.

When a circuit pattern formed on a mask by means of the exposure device is transferred onto a semiconductor wafer, all of defects detected by the technique disclosed in Jpn. Pat. Appln. KOKAI Publication No. 2003-114200 will not give a fatal influence to the wafer-transferred pattern. The influence of detected defects can be neglected in some cases depending on the exposure condition of the numerical aperture of the exposure device and to-be-transferred pattern. Therefore, since the process of precisely grasping the shape of the defect as in this embodiment makes it possible to estimate the degree of influence by the defect at the exposure time, it is extremely important to enhance the production efficiency of masks.

Further, in this embodiment, the process of outputting a defect shape that cannot be realized by the technique disclosed in Jpn. Pat. Appln. KOKAI Publication No. 2007-171640 explained before can be realized. Therefore, in a case other than the transfer risk of 0 or 100%, whether a pattern can be precisely transferred or not can be determined.

When this embodiment is applied to a method of manufacturing a semiconductor device, mask defects can be detected with high efficiency in the semiconductor device-manufacturing process. Accordingly, it is possible to improve the manufacturing yield of semiconductor devices.

(Second Embodiment)

Figure 8:
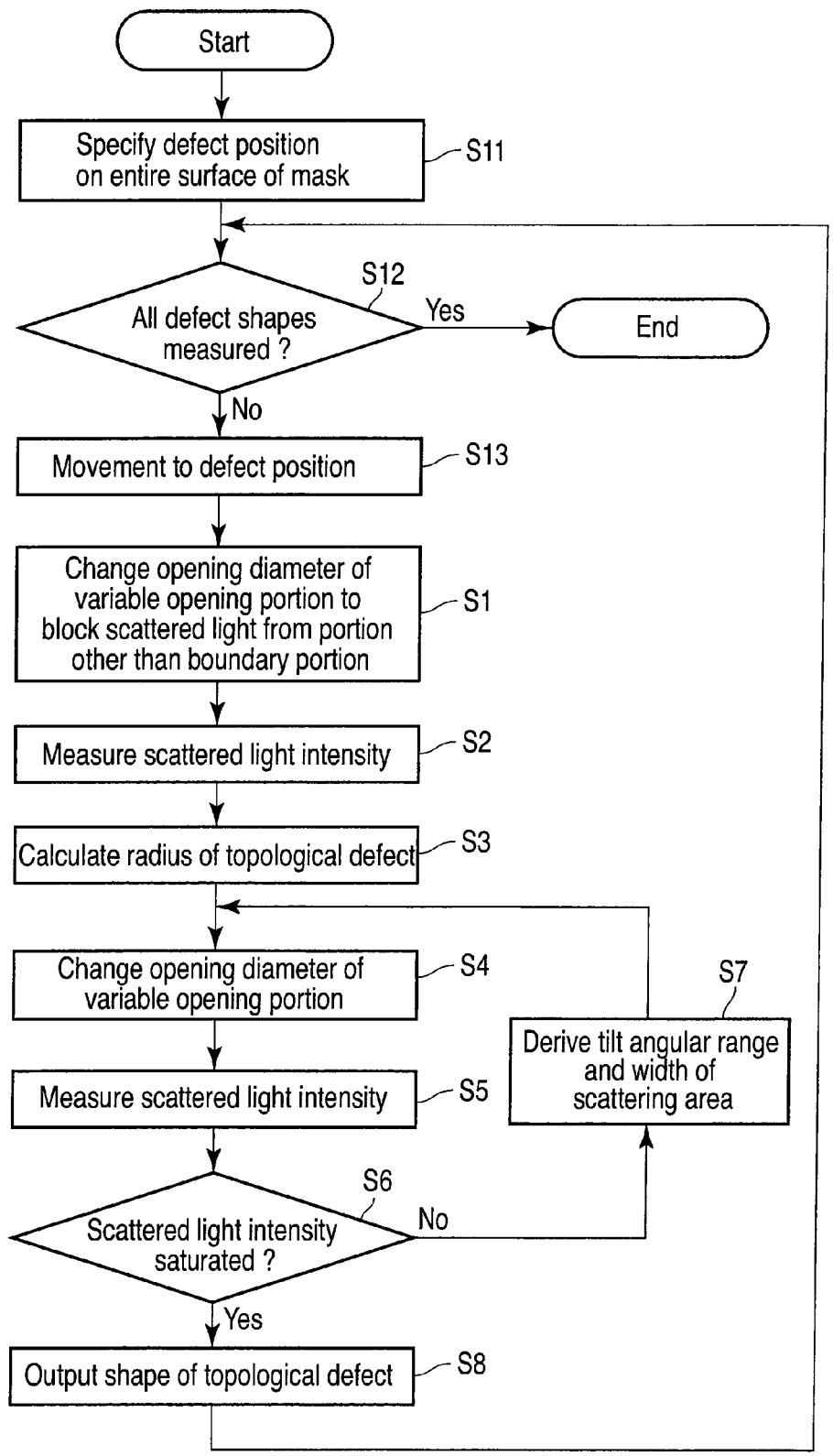
FIG. 8 is a flowchart for illustrating a mask defect shape measurement method according to a second embodiment.

Next, a mask phase defect shape measurement method according to a second embodiment of this invention is explained with reference to the flowchart of FIG. 8. The configuration of a device used in this embodiment is the same as that shown in FIG. 1.

First, before the shape measurement for a phase defect on a mask is made, the presence or absence and the position of the phase defect on the mask are detected (step S11). A measurer sets a blank mask 204 on the mask stage 205 of the device of FIG. 2. Light emitted from the light source 201 is applied to the blank mask surface via the elliptical mirror 202 and plane mirror 203. When the variable aperture stop 206 is adequately set and scattered light is detected by means of the detector 209, the presence of a defect on the blank mask 209 is determined. Then, the positional coordinates of the stage 205 and the pixel position of an image obtained by the detector 209 are stored in the personal computer 210. Subsequently, all of the positions of defects existing on the blank mask are specified by moving the mask stage 209 and scanning the entire surface of the blank mask.

Next, whether or not defect shapes have been measured in all of the defect positions is determined (step S12). If the above measurement is not completed, the next defect position is set by moving the mask stage 205 (step S13) and a defect shape is measured by means of the same method (steps S1 to S8) as that of the first embodiment. Then, if the defect shape measurement in the above defect position is terminated, the process returns to step S12 and the next defect position is set. The process of measuring the defect shape is performed in all of the defect positions.

According to this embodiment, the same effect as that of the first embodiment can of course be attained and determination of the defect position on the blank mask and defect shape measurement can be performed by means of the same device. Therefore, the effect that the time required for defect position determination and shape measurement can be markedly reduced can be attained.

(Modification)

This invention is not limited to the above embodiments. In the embodiments, the mask phase defect shape measurement is made, but it becomes possible to determine the quality of a mask by further developing the above measurement. That is, if the defect shape permissible range is previously set, the quality of a mask can be determined by comparing the measured defect shape with the shape permissible range. In addition, the method for determining the quality of a mask is applicable to a method for manufacturing a semiconductor device. When this application is performed, it is possible to contribute to a decrease in the manufacturing cost of semiconductor devices.

The configuration of the device that detects scattered light from a mask is not limited to the configuration using the variable aperture stop, light shielding portion, concave mirror, convex mirror and the like as shown in FIG. 2 and any configuration can be used if scattered light in a preset angular range can be detected. Further, the angular range can be changed by tilting the mask. In addition, this invention can be variously modified without departing from the scope of this invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A mask defect measurement method for measuring a shape of a phase defect existing on an exposure mask, comprising:

previously deriving an angular range in which width of a scattering area on the phase defect is predictable within an angular range in which inspection light having a desired wavelength incident on the mask is scattered by the phase defect on the mask and measuring intensity of light scattered in the angular range, calculating a radius of the phase defect based on the measured scattered light intensity by using a previously set relational expression, changing the angular range of scattered light to be measured and remeasuring scattered light intensity in the changed angular range, calculating a scattering cross-sectional area based on the remeasured scattered light intensity by using a relational expression of the predetermined scattered light intensities and scattering cross-sectional areas, repeatedly performing a process of remeasuring the scattered light intensity and calculating the scattering cross-sectional area until the remeasured scattered light intensity is saturated, and determining a shape of the phase defect on the mask by using the calculated radius of the phase defect and each of the calculated scattering cross-sectional areas according to a predetermined phase defect shape model.

2. The method according to claim 1, wherein the scattered light intensity and scattering cross-sectional area are set in a proportional relationship as a relational expression used for calculating the scattering cross-sectional area and a proportional coefficient is previously set.

3. The method according to claim 2, wherein the relational expression used for calculating the scattering cross-sectional area is expressed by $I = S \times R \times I_i$, where I is the reflected light intensity, S is the scattering cross-sectional area, R is the reflectance and $I_i$ is the incident light intensity for each unit area.

4. The method according to claim 1, wherein the phase defect shape model is configured by an area in which a cross-sectional shape of the phase defect is known and an area in which a cross-sectional shape of the phase defect is unknown and a contour of the phase defect is a circle.

5. The method according to claim 1, wherein a scattering cross-sectional area is calculated based on the measured scattered light intensity and the radius of the phase defect is calculated based on the calculated scattering cross-sectional area by using the relational expression of the scattering cross-sectional areas and the predetermined scattered light intensities and the relational expression of the predetermined scattering cross-sectional areas and the radii of the phase defects when the radius of the phase defect is calculated.

6. A method for manufacturing a semiconductor device, comprising:

measuring a defect of a lithography mask in the mask defect measurement method according to claim 1.

7. A mask defect measurement method for measuring a position and shape of a phase defect existing on an exposure mask, comprising:

scanning light on the mask to detect a position in which scattered light is emitted from the mask as the position of the phase defect, previously deriving an angular range in which width of a scattering area on the phase defect is predictable within an angular range in which inspection light having a desired wavelength incident on the mask is scattered by the phase defect on the mask and measuring intensity of light scattered in the angular range when the inspection light is made incident on the mask in the detected defect position, calculating a radius of the phase defect based on the measured scattered light intensity by using a previously set relational expression, changing the angular range of scattered light to be measured and remeasuring scattered light intensity in the changed angular range, calculating a scattering cross-sectional area based on the remeasured scattered light intensity by using a relational expression of the predetermined scattered light intensities and scattering cross-sectional areas, repeatedly performing a process of remeasuring the scattered light intensity and calculating the scattering cross-sectional area until the remeasured scattered light intensity is saturated, and determining a shape of the phase defect on the mask by using the calculated radius of the phase defect and each of the calculated scattering cross-sectional areas according to a predetermined phase defect shape model.

8. The method according to claim 7, wherein position detection of the phase defect is performed on an entire surface of the mask and the phase defect shape is determined based on measurement of the scattered light intensity for each of the detected positions.

9. The method according to claim 7, wherein the scattered light intensity and scattering cross-sectional area are set in a proportional relationship as a relational expression used for calculating the scattering cross-sectional area and a proportional coefficient is previously set.

10. The method according to claim 9, wherein the relational expression used for calculating the scattering cross-sectional area is expressed by $I=S \times R \times I_i$, where I is the reflected light intensity, S is the scattering cross-sectional area, R is the reflectance and $I_i$ is the incident light intensity for each unit area.

11. The method according to claim 7, wherein the phase defect shape model is configured by an area in which a cross-sectional shape of the phase defect is known and an area in which a cross-sectional shape of the phase defect is unknown and a contour of the phase defect is a circle.

12. The method according to claim 7, wherein a scattering cross-sectional area is calculated based on the measured scattered light intensity and a radius of the phase defect is calculated based on the calculated scattering cross-sectional area by using the relational expression of the scattering cross-sectional areas and the predetermined scattered light intensities and the relational expression of the predetermined scattering cross-sectional areas and the radii of the phase defects when the radius of the phase defect is calculated.

13. A method for manufacturing a semiconductor device, comprising:
measuring a defect of a lithography mask in the mask defect measurement method according to claim 7.

14. A mask quality determination method comprising:
previously deriving an angular range in which width of a scattering area on a phase defect is predictable within an angular range in which inspection light having a desired wavelength incident on a mask is scattered by the phase defect on the mask and measuring intensity of light scattered in the angular range, calculating a radius of the phase defect based on the measured scattered light intensity by using a previously set relational expression, changing the angular range of scattered light to be measured and remeasuring scattered light intensity in the changed angular range, calculating a scattering cross-sectional area based on the remeasured scattered light intensity by using a relational expression of the predetermined scattered light intensities and scattering cross-sectional areas, repeatedly performing a process of remeasuring the scattered light intensity and calculating the scattering cross-sectional area until the remeasured scattered light intensity is saturated, determining a shape of the phase defect on the mask by using the calculated radius of the phase defect and each of the calculated scattering cross-sectional areas according to a predetermined phase defect shape model, and determining quality of the mask by comparing the determined defect shape with a predetermined defect shape permissible range.

15. The method according to claim 14, wherein the scattered light intensity and scattering cross-sectional area are set in a proportional relationship as a relational expression used for calculating the scattering cross-sectional area and a proportional coefficient is previously set.

16. The method according to claim 15, wherein the relational expression used for calculating the scattering cross-sectional area is expressed by $I=S \times R \times I_i$, where I is the reflected light intensity, S is the scattering cross-sectional area, R is the reflectance and $I_i$ is the incident light intensity for each unit area.

17. The method according to claim 14, wherein the phase defect shape model is configured by an area in which a cross-sectional shape of the phase defect is known and an area in which a cross-sectional shape of the phase defect is unknown and a contour of the phase defect is a circle.

18. The method according to claim 14, wherein a scattering cross-sectional area is calculated based on the measured scattered light intensity and a radius of the phase defect is calculated based on the calculated scattering cross-sectional area by using the relational expression of the scattering cross-sectional areas and the predetermined scattered light intensities and the relational expression of predetermined scattering cross-sectional areas and the radii of the phase defects when the radius of the phase defect is calculated.

19. A method for manufacturing a semiconductor device, comprising:
determining quality of a lithography mask in the mask quality determination method according to claim 14.

\* \* \* \* \*